US007823809B2

(12) United States Patent
Yamaguchi et al.

(10) Patent No.: US 7,823,809 B2
(45) Date of Patent: *Nov. 2, 2010

(54) ELECTROSTATIC SPRAYING DEVICE

(75) Inventors: Naoki Yamaguchi, Hikone (JP); Koji Asakawa, Hikone (JP); David Edward Wilson, Reisterstown, MD (US); Kazumi Toyama, Kobe (JP); Meei-Lih Lin, Kobe (JP)

(73) Assignees: Panasonic Electric Works Co., Ltd., Osaka (JP); The Procter & Gamble Company, Cincinnati, OH (US)

( * ) Notice: Subject to any disclaimer, the term of this patent is extended or adjusted under 35 U.S.C. 154(b) by 139 days.

This patent is subject to a terminal disclaimer.

(21) Appl. No.: 10/588,779

(22) PCT Filed: Nov. 26, 2004

(86) PCT No.: PCT/JP2004/018000

§ 371 (c)(1),
(2), (4) Date: Aug. 8, 2006

(87) PCT Pub. No.: WO2005/075095

PCT Pub. Date: Aug. 18, 2005

(65) Prior Publication Data

US 2007/0131805 A1 Jun. 14, 2007

(30) Foreign Application Priority Data

Feb. 9, 2004 (WO) ................. PCT/JP2004/001353

(51) Int. Cl.

| | |
|---|---|
| ***B05B 5/00*** | (2006.01) |
| *A62C 13/62* | (2006.01) |
| *A62C 11/00* | (2006.01) |
| *B05B 7/26* | (2006.01) |
| *B05B 7/00* | (2006.01) |
| *A61M 11/00* | (2006.01) |
| *A61M 15/00* | (2006.01) |
| *B65D 35/28* | (2006.01) |
| *B65D 35/00* | (2006.01) |
| *B67D 7/60* | (2006.01) |
| *F04B 17/00* | (2006.01) |
| *F04B 35/04* | (2006.01) |

(52) U.S. Cl. .................... 239/690.1; 239/690; 239/692; 239/704; 239/705; 239/706; 239/707; 239/708; 239/302; 239/308; 239/316; 239/329; 239/330; 239/697; 239/698; 128/200.14; 128/203.12; 222/103; 222/107; 222/386.5; 222/630; 417/410.4; 417/423.7

(58) Field of Classification Search ................. 239/690, 239/706, 708, 690.1, 302, 308, 316, 328, 239/332, 327, 692, 704, 303–305, 329, 330, 239/697–698, 705, 707; 128/203.12, 200.14; 222/103, 107, 386.5, 630; 417/410.4, 423.7
See application file for complete search history.

(56) References Cited

U.S. PATENT DOCUMENTS 2,525,347 A * 10/1950 Gilman .......................... 95/71
3,887,928 A * 6/1975 Ohno et al. .................... 347/55
4,120,015 A * 10/1978 Haller ........................ 361/227
4,248,386 A * 2/1981 Morle ........................ 239/707
4,356,528 A 10/1982 Coffee
4,380,786 A * 4/1983 Kelly ......................... 361/228
4,962,885 A * 10/1990 Coffee ........................... 239/3
5,163,625 A * 11/1992 Takayama et al. ........... 239/703
5,184,778 A * 2/1993 Noakes ....................... 239/691
5,218,290 A * 6/1993 Beckert et al. .............. 324/115
5,221,050 A * 6/1993 Jeffries et al. ............... 239/708
5,337,963 A * 8/1994 Noakes ....................... 239/690
5,512,228 A * 4/1996 Adams et al. ............... 264/152
5,591,412 A * 1/1997 Jones et al. ................. 422/171
5,704,554 A * 1/1998 Cooper et al. ............ 239/690.1
5,725,161 A * 3/1998 Hartle ........................ 239/690
5,788,468 A * 8/1998 Dewa et al. ................. 417/415
5,813,614 A * 9/1998 Coffee ........................ 239/690
5,927,618 A * 7/1999 Jefferies et al. .......... 239/690.1
6,050,498 A * 4/2000 Minoura et al. ............. 239/112
6,311,903 B1 * 11/2001 Gaw et al. .................. 239/690
6,318,647 B1 * 11/2001 Gaw et al. .................. 239/690
6,397,838 B1 6/2002 Zimlich, Jr. et al.

| | | | | |
|---|---|---|---|---|
| 6,460,781 | B1 * | 10/2002 | Garcia et al. | 239/327 |
| 6,595,208 | B1 * | 7/2003 | Coffee et al. | 128/203.12 |
| 6,708,908 | B2 * | 3/2004 | Heldt et al. | 239/700 |
| 6,744,046 | B2 * | 6/2004 | Valaskovic et al. | 250/288 |
| 6,911,132 | B2 * | 6/2005 | Pamula et al. | 204/600 |
| 7,091,430 | B1 * | 8/2006 | Haizima et al. | 200/6 A |
| 2001/0020652 | A1 | 9/2001 | Kadlubowski et al. | |
| 2001/0020653 | A1 | 9/2001 | Wilson et al. | |
| 2001/0023902 | A1 | 9/2001 | Wilson et al. | |
| 2001/0038047 | A1 | 11/2001 | Wilson et al. | |
| 2002/0100815 | A1 * | 8/2002 | Doebler et al. | 239/67 |
| 2004/0057720 | A1 * | 3/2004 | Westerweck et al. | 396/448 |
| 2005/0196301 | A1 * | 9/2005 | Iwasaki | 417/410.4 |
| 2005/0207914 | A1 * | 9/2005 | Tupy | 417/410.1 |
| 2007/0159015 | A1 * | 7/2007 | Lin et al. | 310/71 |

FOREIGN PATENT DOCUMENTS

| | | |
|---|---|---|
| CN | 1335783 | 2/2002 |
| WO | WO-00/38770 | 7/2000 |
| WO | WO 02/055211 A1 | 7/2002 |
| WO | WO 03/072263 A1 | 9/2003 |

OTHER PUBLICATIONS

Examination Report dated Dec. 14, 2007 from a foreign patent office, issued in a counterpart application, along with English translation thereof.

* cited by examiner

*Primary Examiner*—Dinh Q Nguyen
*Assistant Examiner*—Steven M Cernoch
(74) *Attorney, Agent, or Firm*—Cheng Law Group, PLLC

(57) ABSTRACT

An electrostatic spraying device has a capability of confirming that the device is ready for making an electrostatic spraying of the liquid composition on a user's skin. The device includes a nozzle and a pump for dispensing the liquid composition out through the nozzle. An emitter electrode is disposed to electrostatically charge the liquid composition being dispensed for making the electrostatic spraying. The device is provided with a power switch and a selector for selection between a spraying mode and a dripping mode. In the dripping mode, the pump is alone actuated to dispense the liquid composition absent electrostatic charge. In the spraying mode, both of the pump and the emitter electrode are activated to make the electrostatic spraying. Thus, the user can be easy to drip the liquid composition by simply manipulating the selector prior to initiating the electrostatic spraying.

20 Claims, 19 Drawing Sheets

FIG. 21
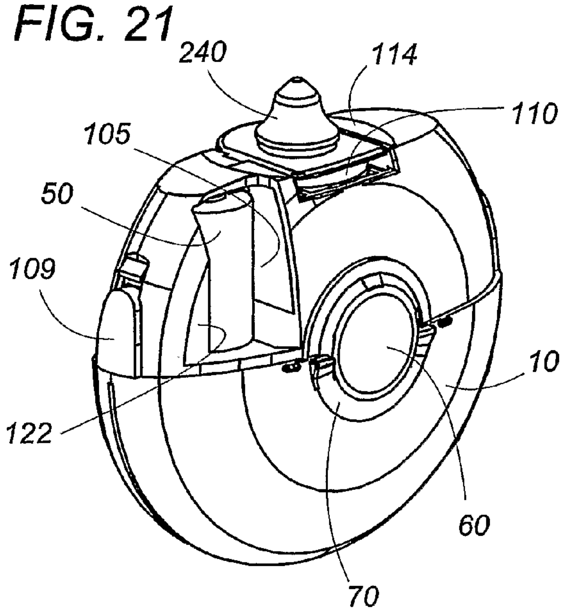
FIG. 22
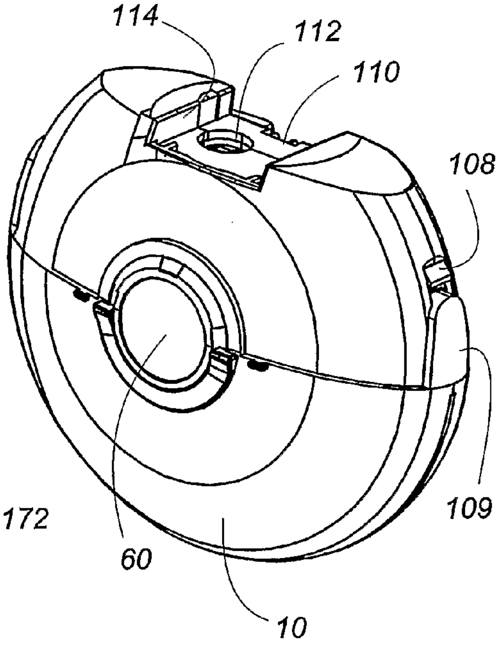
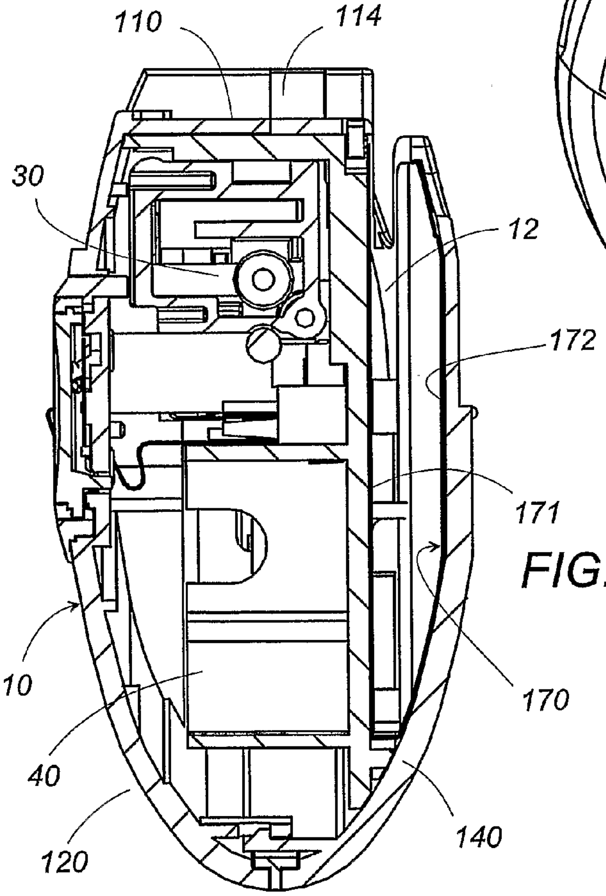
FIG. 23

ELECTROSTATIC SPRAYING DEVICE

TECHNICAL FIELD

The present invention relates to an electrostatic spraying device for personal use, and more particularly to a device for spraying a liquid composition by means of an electrostatic force.

BACKGROUND OF THE INVENTION

WO 03/072263 discloses an electrostatic spraying device having a removable cartridge containing a volume of a liquid composition. The device includes a plunger pump that displaces the liquid out of the reservoir and a nozzle for dispensing the liquid. The nozzle is provided with an emitter electrode which applies a high voltage to the liquid composition being supplied from the reservoir to the nozzle, i.e., electrostatically charge the particles of the liquid composition for spraying the composition on a user's skin by the electrostatic force. In order to start spraying the electrostatically charged liquid composition, the user is required to feed the liquid composition to the nozzle to drip it out of the nozzle and subsequently, after confirming the dripping, to apply the high voltage to the liquid composition being supplied to the nozzle. This is because, if the liquid composition has not yet advanced to the emitter electrode, electrostatical spraying is not likely to start immediately. Thus, the absence of the confirmation might give uncertainty to the user whether or not the device operates normally. However, the confirmation requires the user to take extra steps of ejecting the cartridge out of its position in the main body of the device, manually operating the cartridge to drip the liquid composition prior to energizing the pump and the emitter electrode, and returning the cartridge in position. This is cumbersome and therefore detracting from easy handling of the device. There remains a need for providing a device which enables easy dripping of the liquid composition prior to electrostatically spray.

None of the existing art provides all of the advantages and benefits of the present invention.

SUMMARY OF THE INVENTION

The present invention is directed to an electrostatic spraying device which is capable of spraying the liquid composition successfully only through a simplified step of confirming that the liquid composition is ready for being immediately sprayed electrostatically. The electrostatic spraying device in accordance with the present invention is configured and disposed to electrostatically charge and dispense the liquid composition from a supply to a point of dispense. The device includes an actuator, a high voltage generator to provide a high voltage, a power source to activate the actuator and the high voltage generator, a reservoir to contain the supply of the liquid composition, and a dispensing unit. The dispensing unit is provided to spray the liquid composition and includes a pump which is mechanically connected to the actuator to be driven thereby. An emitter electrode is included in the dispensing unit to be electrically connected to the high voltage generator in order to electrostatically charge the liquid composition. Also included in the dispensing unit is a nozzle that is disposed at the point of dispense for dispensing the liquid composition. The device further includes a switch for manipulating the power source. One characterizing feature of the present invention resides in that a selector is included to provide a spraying mode and a dripping mode selectively in response to the switch being manipulated. The dripping mode defines a mode in which the pump is alone actuated to dispense the liquid composition out through the nozzle absent electrical charge, and the spraying mode defines another mode in which the pump as well as the emitter electrode are simultaneously activated to dispense the liquid composition out through the nozzle with the liquid composition being electrically charged prior to exiting the nozzle. Thus, the user can easily drip the liquid composition by simply manipulating the selector prior to initiating the electrostatic spraying, which assures easy handling of the device and the successful spraying.

In a preferred embodiment, a housing is provided to carry the actuator, the actuator, the high voltage generator, the power source, the switch, and the selector.

Preferably, the selector is exposed on the exterior of the housing to be manipulated by the user's finger, and is movable between a dripping position defining the dripping mode and a spraying position defining the spraying mode. The selector surrounds the switch in immediately adjacent relation thereto and rotatable about an axis between the dripping position and the spraying position. Thus, the selector and the switch can be easily manipulated by a single finger, i.e., a thumb of the user's hand grasping the housing for enhanced convenience of operating the device.

The selector may have a lock position which prohibits the motor and the emitter electrode from being activated, in order to prevent an unintended and accidental operation of the device.

It is also preferred that the housing is formed on its exterior with an indicator which indicates which one of the dripping mode and the spraying mode is selected for easy confirmation by the user.

Alternately, the selector may be of a pressure-responsive type which is actuated by the switch to give the dripping mode in response to the switch handle being pressed to a first extent, and give the spraying mode in response to the switch being pressed to a second extent greater than the first extent.

Further, the spraying mode may be arranged to start activating the pump after a short delay from activating the high voltage generator. In view of a possible delay in generating a stable voltage output from the high voltage generator, the pump is controlled to supply the liquid composition only after the emitter electrode sees the stable high voltage output. Thus, the liquid composition can be charged to an intended level as soon as it is supplied from the reservoir to the dispensing unit, thereby assuring optimum performance of electrostatically applying the liquid composition.

Still further, the spraying mode may be arranged to include monitoring of the voltage output from the high voltage generator and to cease activating the high voltage generator and the pump when the monitored voltage output exceeds a critical level as indicative of an unallowable corona discharging at the emitter electrode, thereby assuring the safe operation of the device.

These and still other features, aspects, and advantages of the present invention will become more apparent from the following detailed explanation of preferred embodiments when taken in conjunction with the attached drawings.

BRIEF DESCRIPTION OF THE DRAWINGS

While the specification concludes with claims particularly pointing out and distinctly claiming the invention, it is believed that the present invention will be better understood from the following description of preferred, nonlimiting embodiments and representations taken in conjunction with the accompanying drawings in which:

FIG. 21 is a perspective view of the above device with the inner cover removed;

FIG. 22 is a perspective view of the above device shown with the cartridge and an inner cover removed;

FIG. 23 is a vertical section of the device corresponding to FIG. 22;

DETAILED DESCRIPTION OF THE INVENTION

Figure 1:
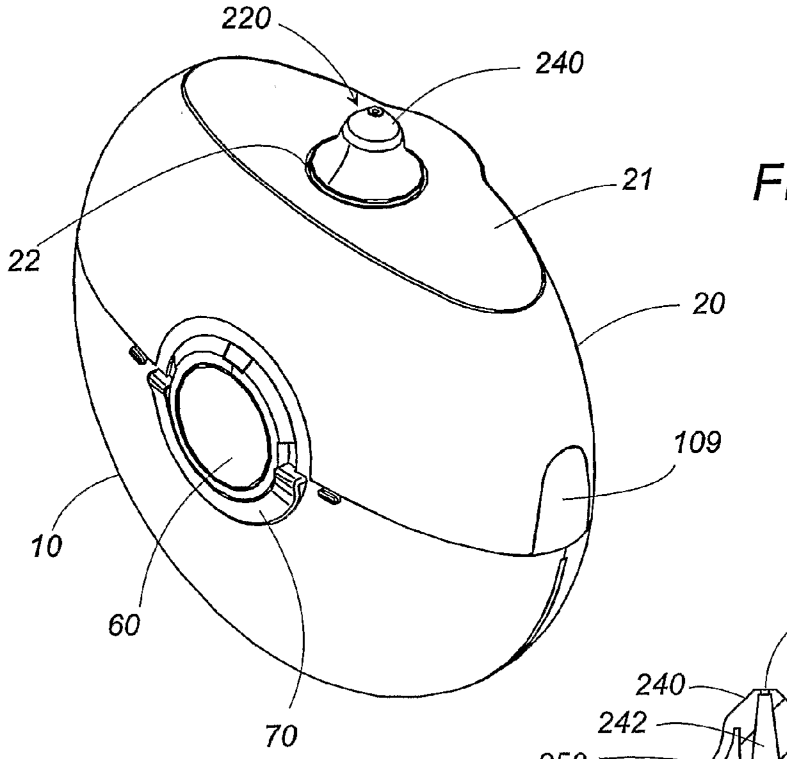
FIG. 1 is a perspective view of an electrostatic spraying device in accordance with a preferred embodiment of the present invention.

Now referring to FIGS. 1 to 7, there is shown an electrostatic spraying device in accordance with a preferred embodiment of the present invention. The device is configured into a self-contained portable structure that is compact enough to be easily carried with. The device is basically composed of a main body housing 10 and a removable cartridge 200 containing a volume of a liquid composition to be electrostatically sprayed according to a mechanism already disclosed in WO 01/12336, WO 01/12335, US 2001-0020653A, US 2001-0038047A, US 2001-0020652A, US 2001-0023902A, and WO 03/072263, incorporated herein by reference. The liquid composition utilized in the device include those disclosed in WO 03/072263, also incorporated herein by reference, i.e., an emulsion having conductive and insulating phases, although not limited thereto.

The housing 10 is dimensioned to be grasped by a user's hand and incorporates an electric motor 30, a high voltage generator 40, and a battery 50, i.e., a power source for activating the motor and the high voltage generator 40. The motor 30 actuates a dispensing unit 220 provided on the side of the cartridge 200 to dispense the liquid composition, while the high voltage generator 40 applies a high voltage of 1000 volts or more to the liquid composition being dispensed for electrically spraying the liquid composition on a user's. The housing 10 is formed with a concavity 12 for receiving a reservoir 210 of the cartridge 200 containing the liquid composition. In a preferred embodiment, an inner cover 20 is detachably fitted over the upper end of the housing 10 to hold therebetween the dispensing unit 220 of the cartridge 200. In another preferred embodiment, an outer cover 26 is detachably fitted over the inner cover 20 to conceal therebehind the dispensing unit 220 for protection thereof when the device is not in use.

The cartridge 200 is preferably composed of the reservoir 210 and the dispensing unit 220. The reservoir 210 may be suitably made of a plastic material which is deformable according to the contents of the liquid composition. The reservoir 210 may be made by the same resilient material, or combination of a rigid material and resilient material. An example of commercially available material suitable for providing the reservoir is the laminated film of VM-PET (Vacuum Metalised Polyethylene Terephthalate) having a thickness of 12 microns and LLDPE (Linear Low Density Polyethylene) having a thickness of 60 microns. Commercially available films are GLAE by Toppan for VM-PET, and FCS by Tocello for LLDPE. The reservoir may also be made of conductive material and being electrically connected to the high voltage generator so that the liquid composition therein is provided with more less a common electric potential.

Figure 2:
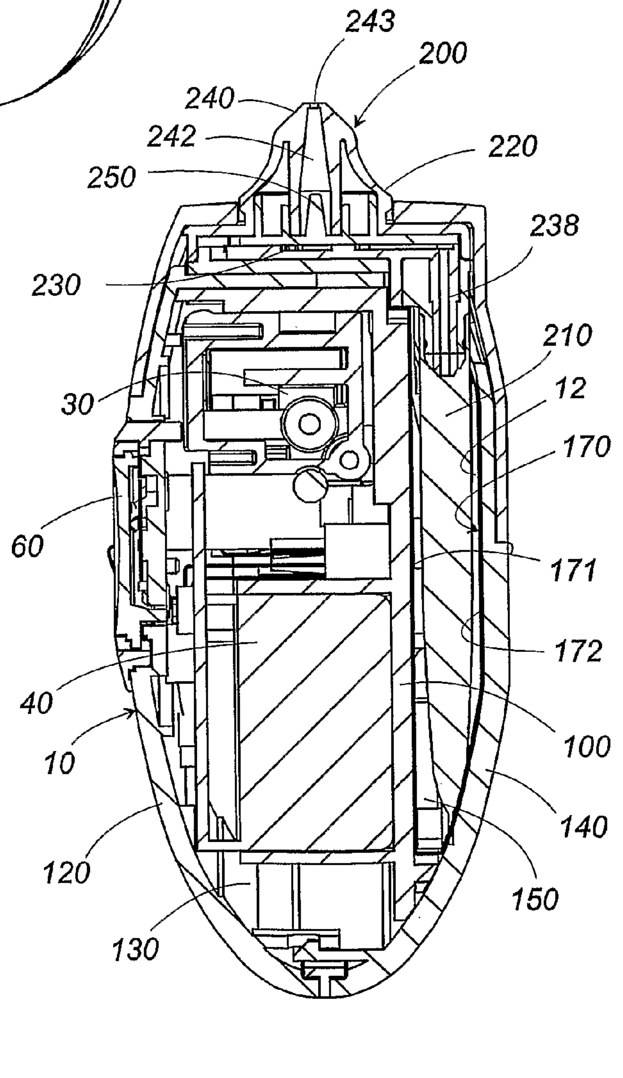
FIG. 2 is a vertical section of the device of FIG. 1.
Figure 3:
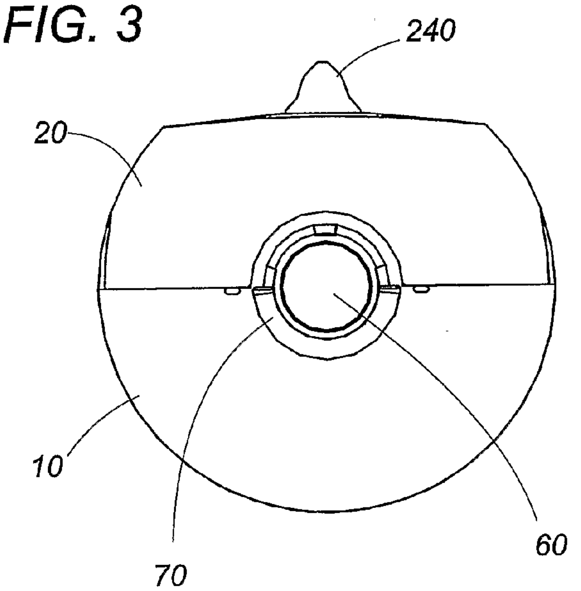
FIG. 3 is a front view of the device of FIG. 1.
Figure 4:
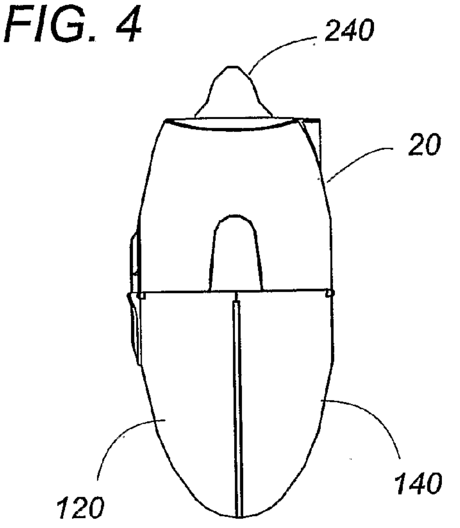
FIG. 4 is a side view of the above device.

As best shown in FIGS. 6 to 9, in a preferred embodiment the dispensing unit 220 includes a pump 230 and a nozzle 240 which are integrated into a single structure. The pump 230 is a gear pump having a flat base 231 molded from a plastic material and formed with a plug 232 for detachable insertion into a fitment 212 secured to a mouth of the reservoir 210. The pump 230 includes a metal plate 270 mounted in the base 231 of the molded plastic. The metal plate 270 is formed in its upper surface with a pump chamber receiving a pair of intermeshing gears 234, an inflow channel 236 extending from within the plug 232 to the chamber, and an outflow channel 237 extending from the chamber to the nozzle 240. The pump chamber as well as the channels 236 and 237 are sealed by an emitter electrode 250 secured between the base 231 and the nozzle 240. The gears 234 are arranged to have their individual rotation axes extending perpendicular to the plane of the base 231, realizing a flat pump structure sufficient to be capable of being disposed between the reservoir 210 and the nozzle 240 only at a minimum extra dimension with respect to the height or length of the dispensing unit 220. One of the gears 234 is coupled to a joint 238 projecting on the lower face of the base 231 for detachable driving connection with the motor 30 disposed within the housing 10. As the gears are driven to rotate, the liquid composition is sucked up from the reservoir 210 through the inflow channel 236 and expelled through the outflow channel 237 to the nozzle 240. Preferably, the nozzle 240 is molded from a compatible plastic material as the base 231 to have an internal nozzle pathway 242 extending from the bottom center to an apex 243, as best shown in FIG. 2.

The emitter electrode 250 is disposed between the base 231 of the pump 230 and the bottom 241 of the nozzle 240 in order to apply the high voltage to and charge the liquid composition being dispensed through the nozzle 240. In a preferred embodiment, the emitter electrode 250, which is connected to receive the high voltage from the high voltage generator 40 in the housing 10, includes a center antenna 251 and a coaxial cylinder 252. The center antenna 251 extends into the nozzle pathway 242 to charge the liquid composition being dispensed in cooperation with the cylinder 252 that is provided to surround the nozzle pathway 242 to avoid the undesired corona discharging for suitable electrostatic spraying. The top end of the center antenna 251 is receded from the apex 243 of the nozzle 240 to give a sufficient insulation distance therebetween.

Figure 11:
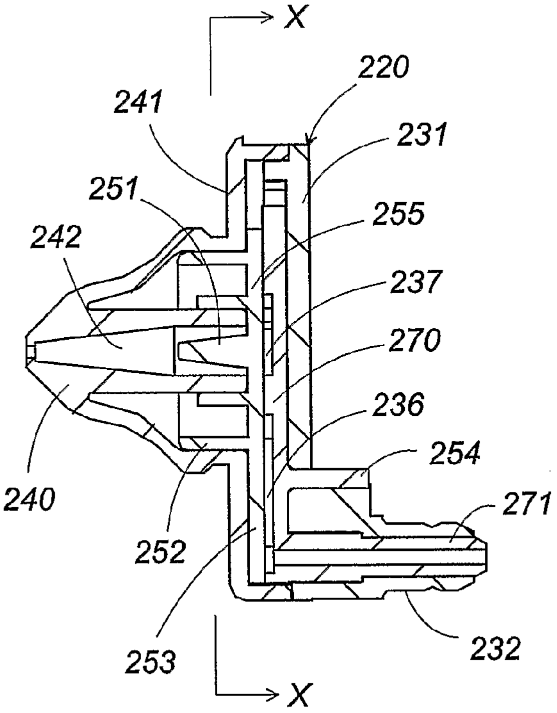
FIG. 11 is a sectional view of the dispensing unit.
Figure 12:
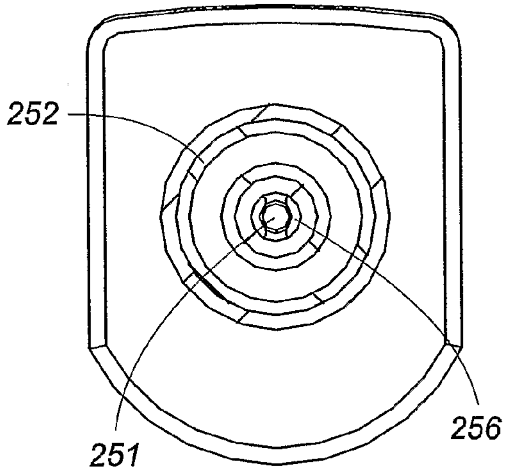
FIG. 12 is a section take along line X-X of FIG. 11.
Figure 13:
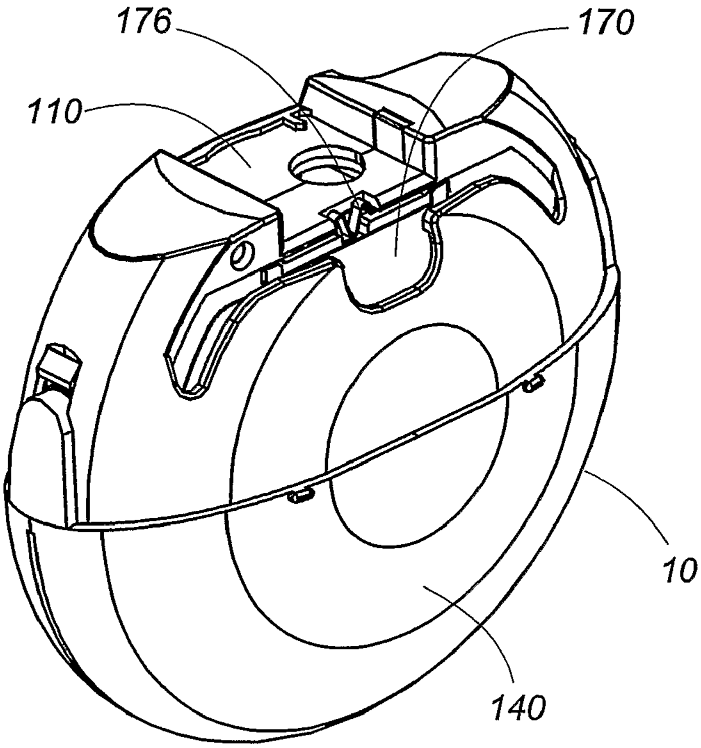
FIG. 13 is a perspective view of a main body housing of the device.
Figure 14:
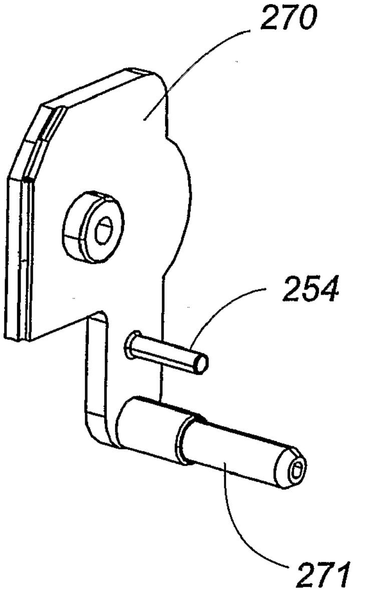
FIG. 14 is a perspective view of a metal plate forming a part of the dispensing unit.
Figure 15:
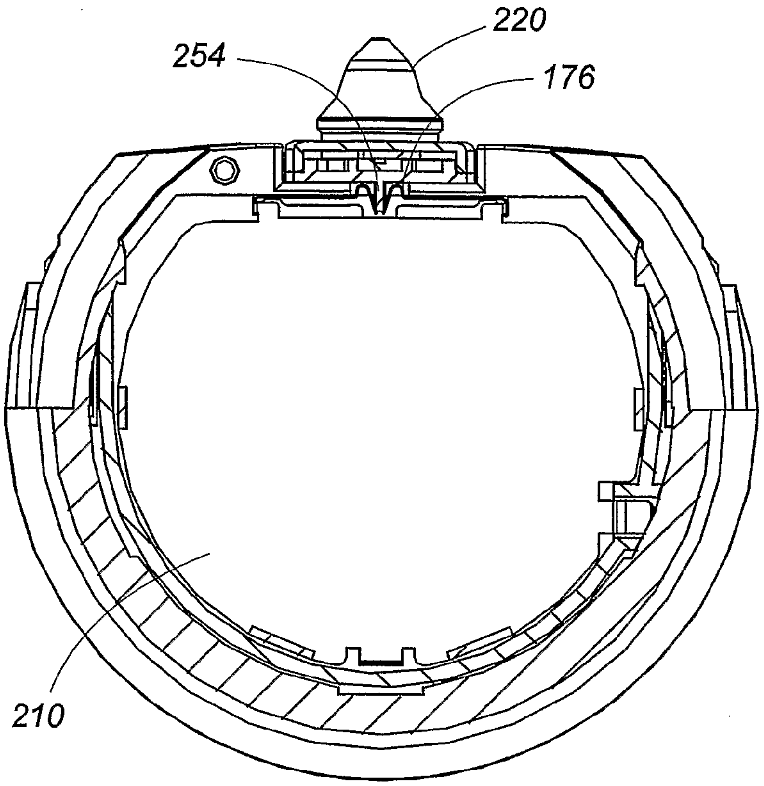
FIG. 15 is a partial rear section showing an electrical connection between the dispensing unit and a voltage terminal provided on the side of the housing.
Figure 16:
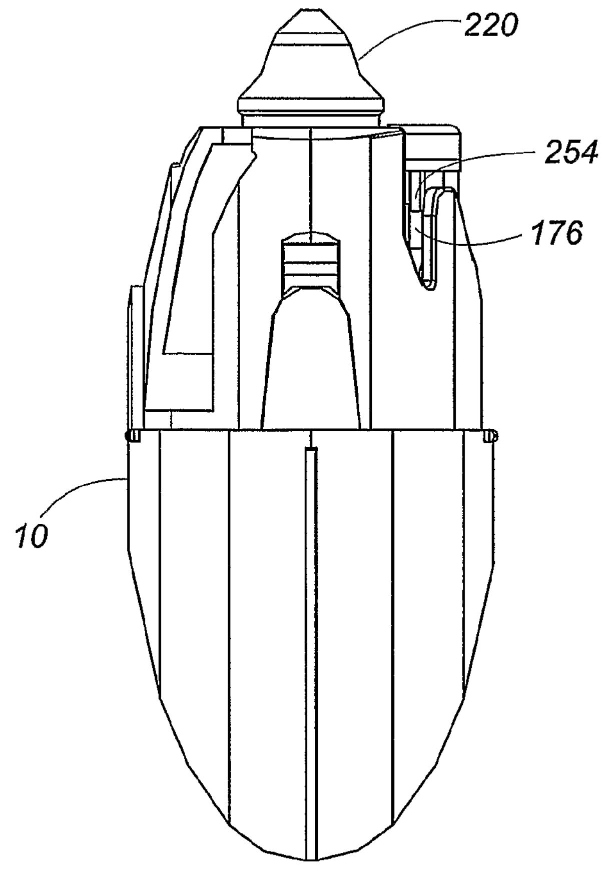
FIG. 16 is a partial vertical section showing the electrical connection between the dispensing unit and the voltage terminal.

As best shown in FIGS. 13 to 16, the metal plate 270 is formed integrally with a pin 254 which projects through the base 231 for detachable electrical connection with a voltage terminal 176 provided on the side of the housing 10 to relay the high voltage to the emitter electrode 250. Turning back to FIGS. 6 and 7, the emitter electrode 250 also includes a flat bottom 253 that is placed over the base 231 to seal the pump. The flat bottom 253 and the metal plate 270 are cooperative to charge the liquid composition within the pump in order to avoid undesired current flow within the liquid composition in the pump which would otherwise cause deterioration of the liquid composition. As shown in FIGS. 11 and 12, the cylinder 252 is connected to the antenna 251 by a rim 255. The rim 255 is formed with a plurality of slots 256 that communicate with the outflow channel 237 of the pump for passing the liquid composition from the pump to the nozzle pathway 242.

Figure 5:
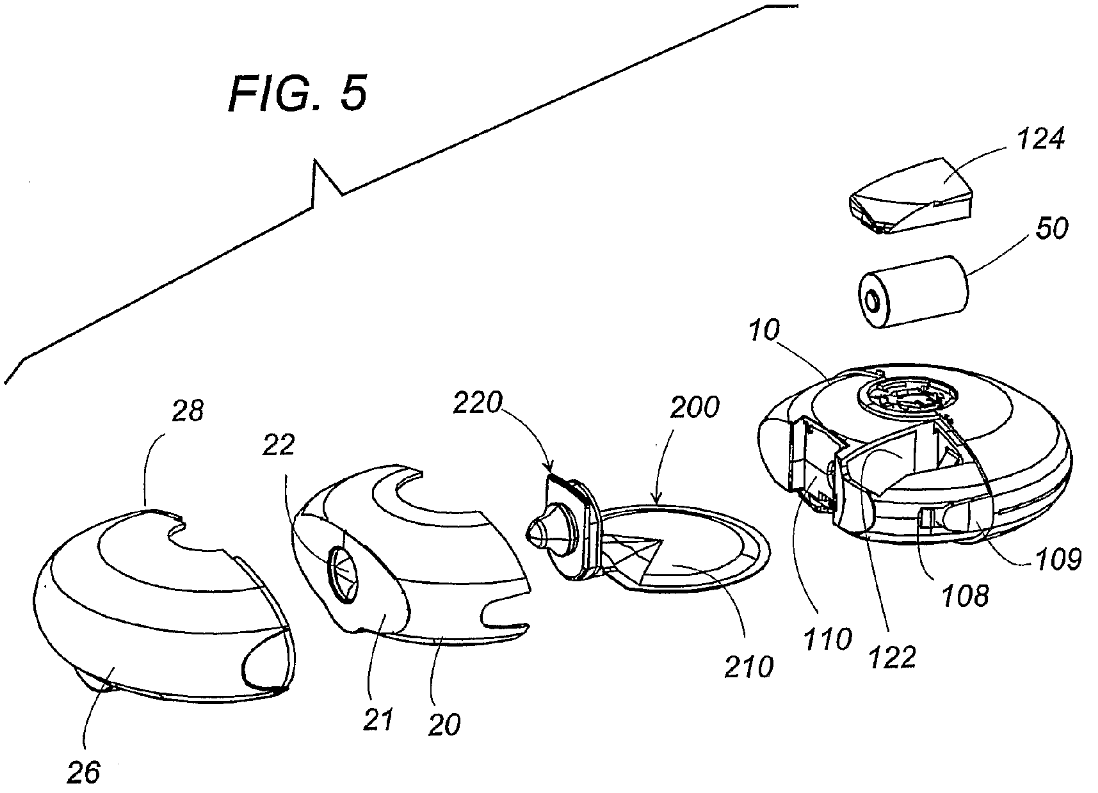
FIG. 5 is an exploded perspective view of the above device.
Figure 6:
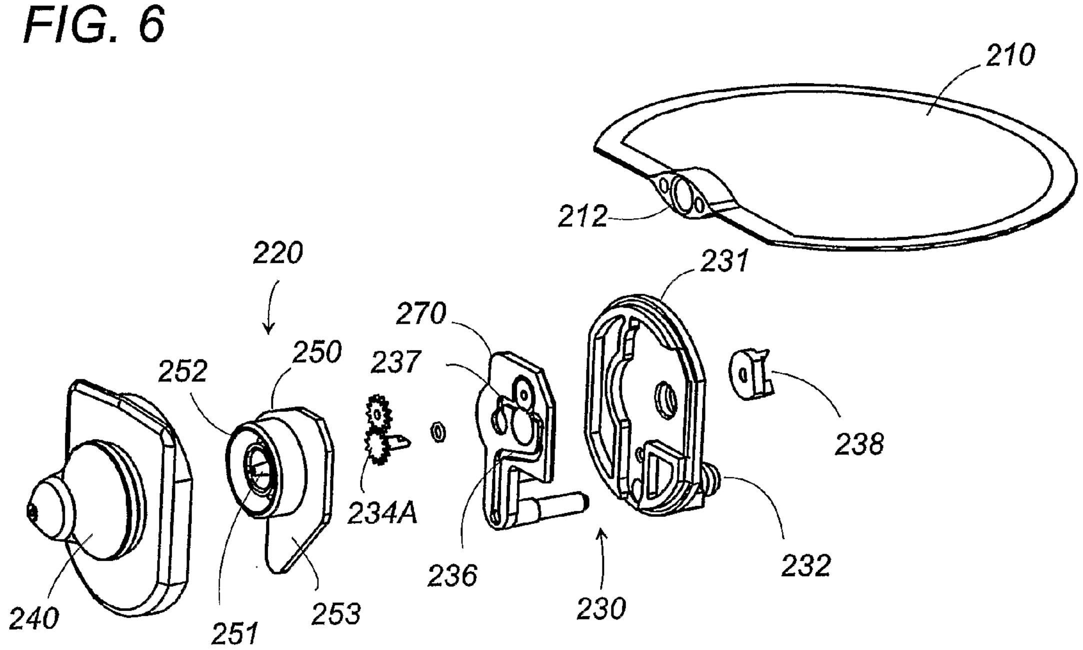
FIGS. 6 to 8 are respectively exploded perspective views of a removable cartridge utilized in the above device.
Figure 7:
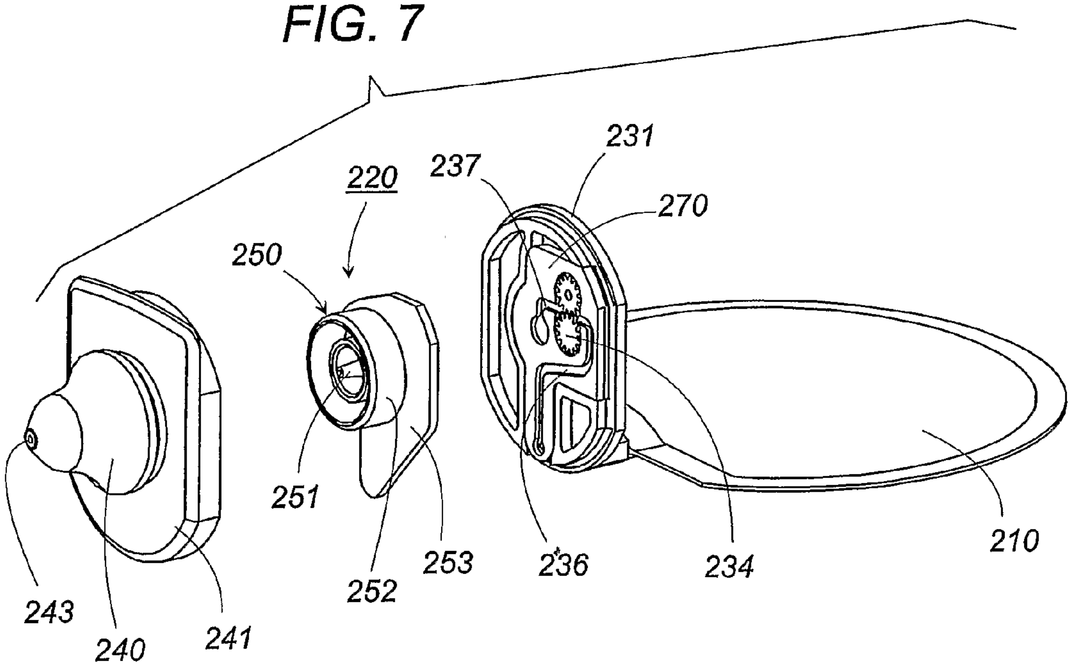
Figure 8:
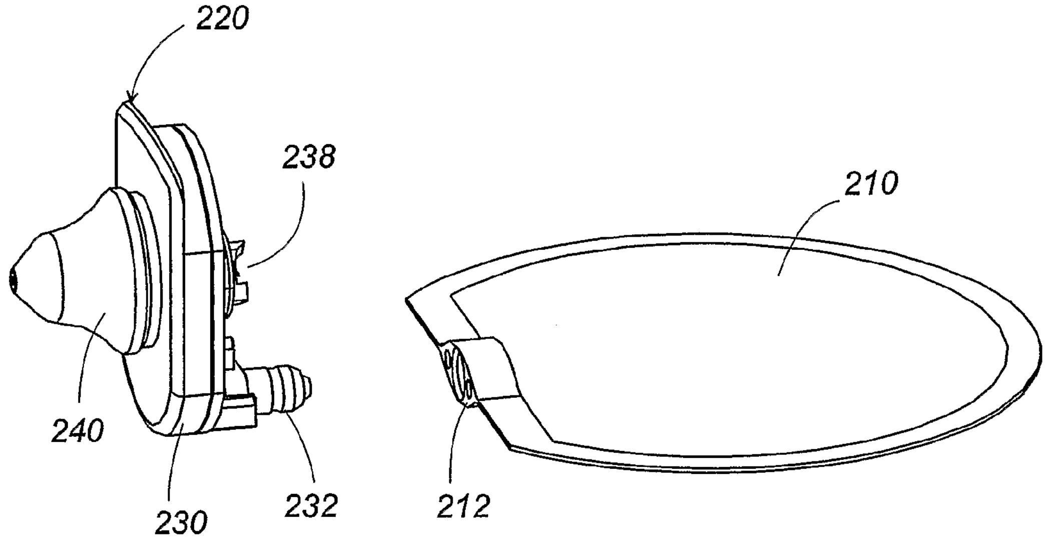
Figure 9:
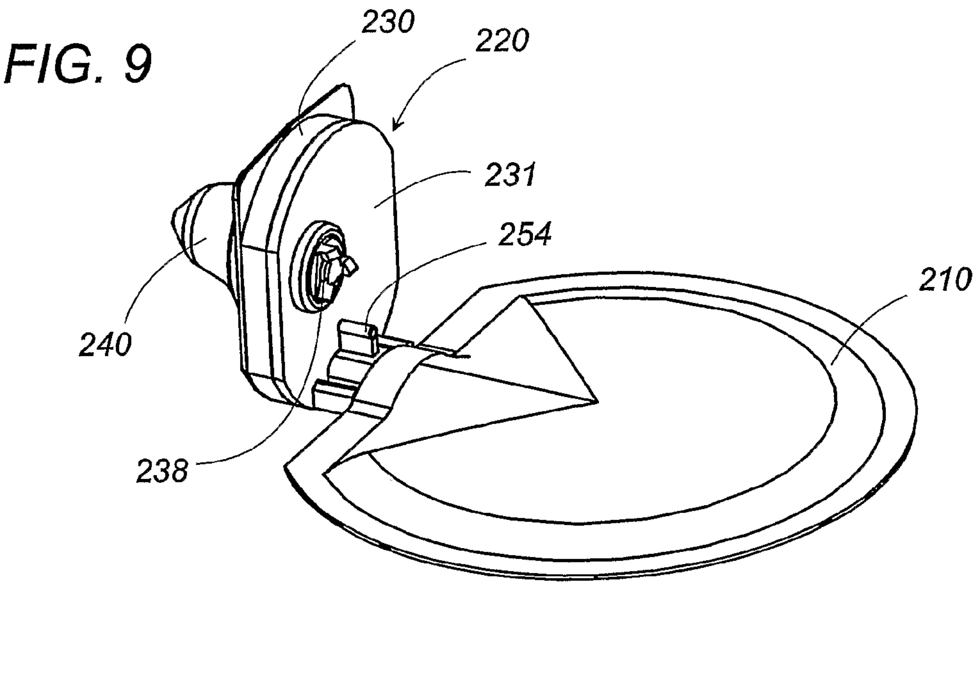
FIG. 9 is a perspective view of the cartridge of FIG. 8 as viewed from the bottom.
Figure 10:
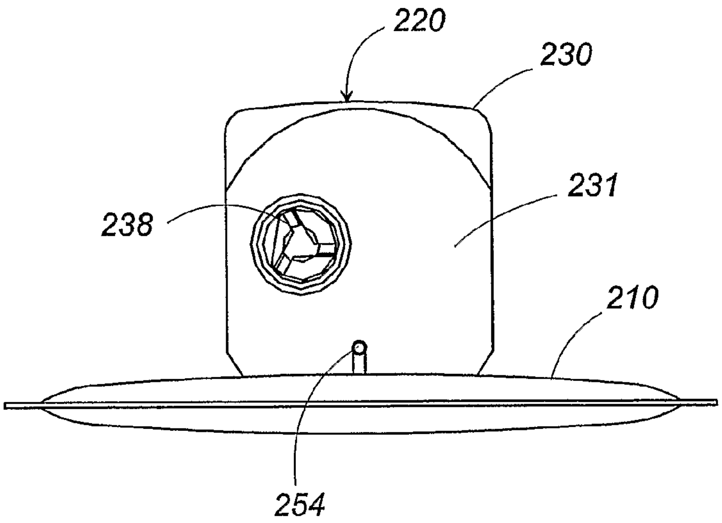
FIG. 10 is a bottom view of the cartridge of FIG. 9.
Figure 17:
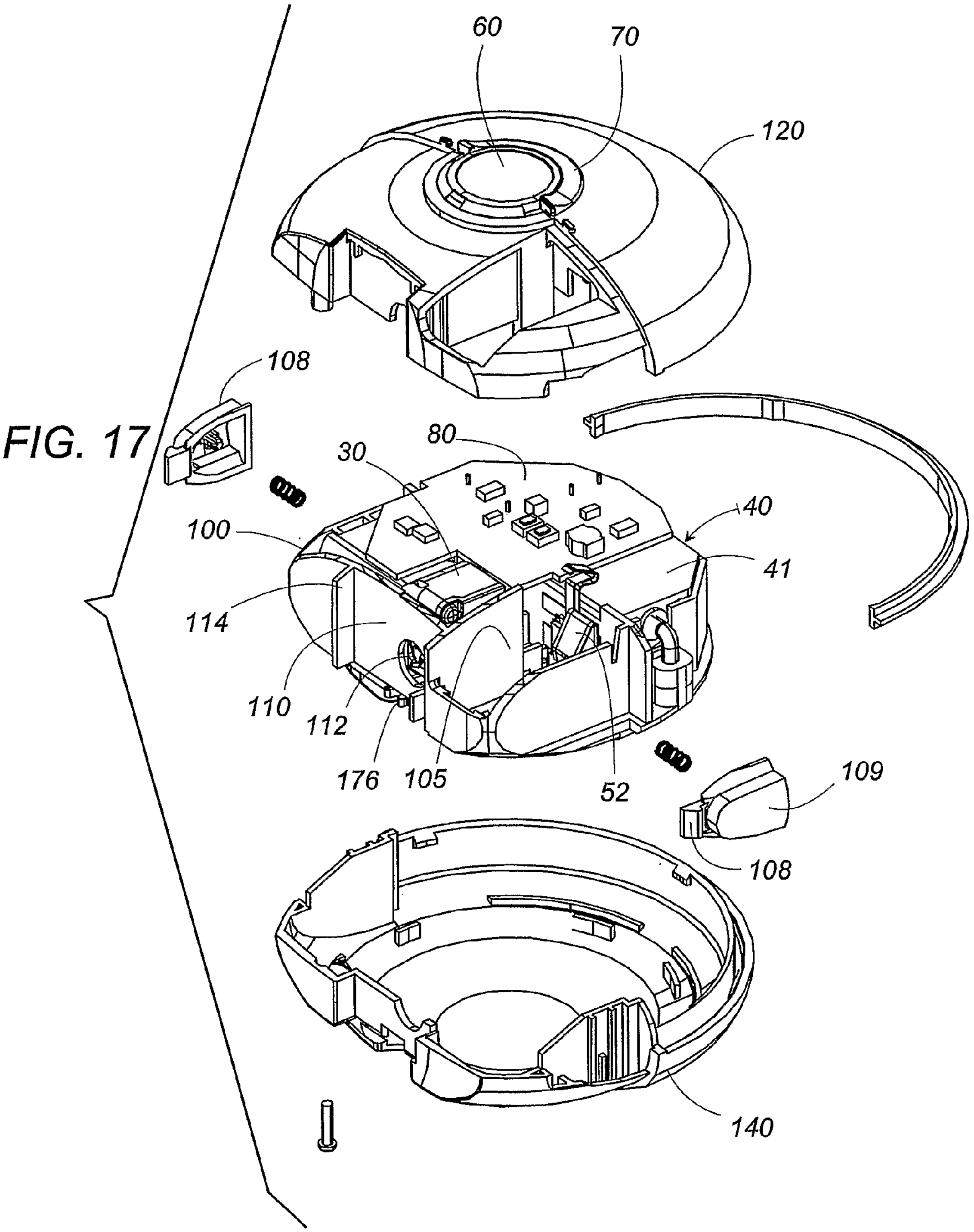
FIG. 17 is an exploded perspective view of the housing of the device.
Figure 18:
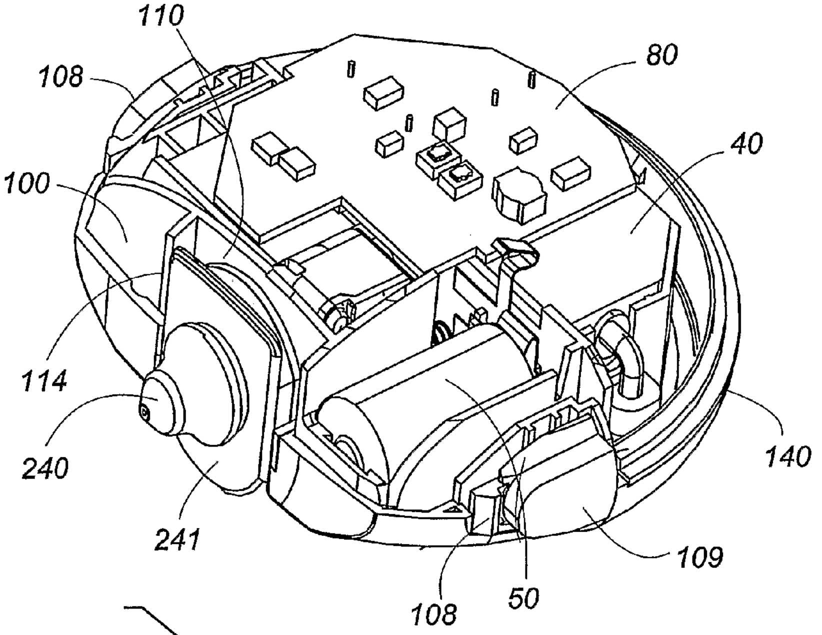
FIG. 18 is a perspective view of the device shown with a front shell of the housing removed.
Figure 19:
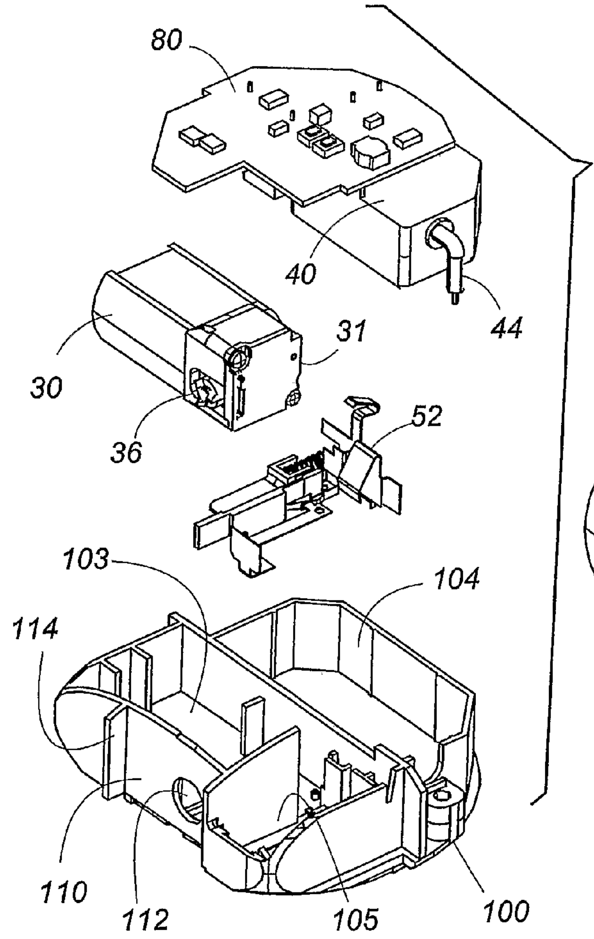
FIG. 19 is an exploded perspective view illustrating a center frame of the housing, a motor and a high voltage generator mounted on the frame in accordance with the preferred embodiment of the present invention.
Figure 20:
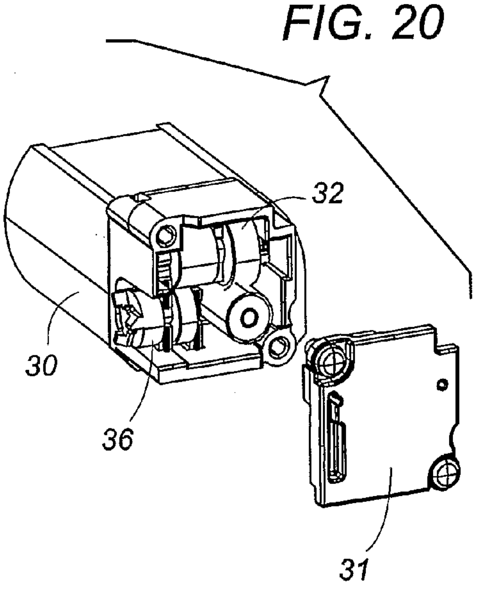
FIG. 20 is an exploded perspective view showing the motor and its associated parts accommodated within the housing in accordance with the preferred embodiment of the present invention.

As shown in FIG. 17, the housing 10 may be shaped into a generally flat disc, and thus basically composed of a center frame 100, a front shell 120, and a rear shell 140 all being molded from a dielectric plastic material and assembled together into a unitary structure to form a front compartment 130 and a rear compartment 150 on opposite faces of the frame 100, respectively behind the front and rear shells. When taking such generally flat disc shape, the front compartment 130 accommodates therein the motor 30, the battery 50, and the high voltage generator 40 which are all supported on the frame 100, while the rear compartment 150 constitutes the concavity 12 for receiving the reservoir 210. The frame 100 is formed on its front face with individual sections 103, 104, and 105 respectively for mounting the motor 30, the high voltage generator 40, and the battery 50, as shown in FIGS. 18 and 19. The motor 30 is received in the section 103 together with a gearbox 31. The high voltage generator 40 is composed of a transformer 41 and various electric components mounted on a printed board 80. The transformer 41 is packed into an insulated module fitted in the section 104. In that the transformer 41 occupies much more space than the motor 30 and battery 50, the housing is designed to arrange the transformer 41, the motor 30, and the battery 50 in compact. That is, the transformer 41 is accommodated within the lower part of the front compartment, while the motor 30 and the battery 50 are accommodated within the upper part of the front compartment in side-by-side relation with each other such that the motor and the battery are arranged in stack with the transformer with respect to a vertical axis of the housing 10. The section 105 receives, in addition to the battery 50, a terminal fixture 52 having leads for electrical connection of the battery 50 to the motor 30 and the high voltage generator 40 through a power switch 60 and a control circuit formed on the printed board 80. As shown in FIG. 20, the gearbox 31 includes a reduction gear set 32 through which the motor output is transmitted to an actuator 36 provided for detachable driving connection to the joint 238 of the pump 230 on the side of the cartridge 200. Preferably, the actuator 36 is disposed immediately below a mount 110 formed at the upper end of the frame 100 and is accessible through an opening 112 in the mount 110, as shown in FIGS. 22 and 23. The mount 110 is somewhat recessed for retaining the dispensing unit 220 thereon when the cartridge 200 is attached to the housing 10. The mount 110 is cooperative with adjacent side walls 114 to define a positioning means for the cartridge. Preferably, a pair of hooks 108 is attached on the opposite sides of the frame 100 to constitute a positioning means for detachably holding the inner cover 20 on the housing 10. The hook 108 has a release button 109 which releases the inner cover 20 upon being pressed. As seen in FIGS. 1 and 5, the inner cover 20 may have a flat top 21 formed with a center window 22 through which the nozzle 240 projects when the inner cover 20 is placed over the top half of the housing 10 with the cartridge 200 attached to the housing 10. The periphery of the window 22 constitutes a retainer ring that holds the flat nozzle bottom 241 on the mount 110 at the upper end of the housing 10. As shown in FIG. 21, the front shell 120 is formed with a window 122 which communicates with the section 105 for replacement of the battery 50. Thus, the battery 50 can be easily replaced by simply removing the inner cover 20 as well as a lid 124 of the window 122. The lid 124 may be eliminated from the device for simplicity.

The rear compartment 150 may be accommodated with a field electrode which surrounds the reservoir 210 to give the same electrical potential to the liquid composition within the reservoir 210 and to the liquid composition within the dispensing unit 220 for keeping the entire liquid composition free from seeing the electric current which may deteriorate the liquid composition. Such deterioration is particularly seen in emulsion compositions and compositions having particles dispersed therein.

Figure 24:
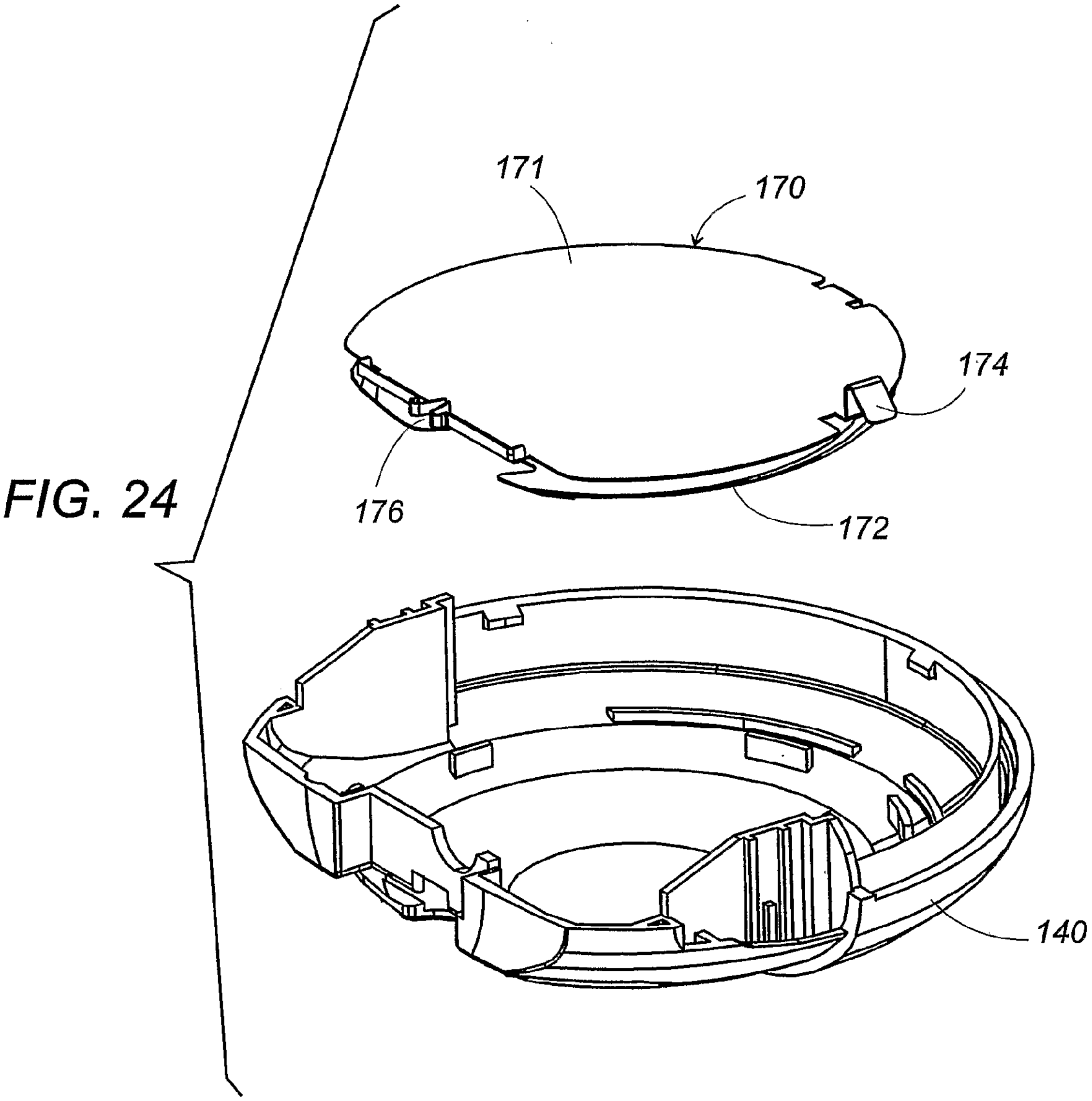
FIG. 24 is an exploded perspective view of parts forming a field electrode and associated parts of the above device.

As best shown in FIGS. 23 and 24, in one embodiment, the field electrode 170 is composed of a first plate 171 and a second plate 172 both made of an electrically conductive metal and shaped to define therebetween the concavity 12 surrounding the entire area of the reservoir 210. The plates 171 and 172 are electrically connected to each other at their peripheries, and are secured to the frame 100 and the rear shell 140. In order to receive the high voltage, the plate 171 is formed to have a lug 174 which extends through the frame 100 for electrical connection with a terminal 44 of the high voltage generator 40. The plate 171 is also formed with the voltage terminal 176 in the form of a spring catch for detachable connection with the pin 254 of the dispensing unit 220, as explained hereinabove.

It is noted in this connection that the metal plate 270 and the 250 of the dispensing unit 220 are electrically connected to the field electrode 170 and therefore act as additional field electrode covering the pump. Also, the metal plate 270 is formed with a metal tube 271 which is inserted into the plug 232 to charge the liquid composition within the plug, and therefore acts also as a further field electrode. Thus, the liquid composition is electrically charged along the entire path from the reservoir 210 to the nozzle 240. Instead of using the metal tube 271, it is equally possible to provide an extension which extends from at least one of the plates 171 and 172 and projects outwardly from the concavity to cover the plug 232 and the adjacent part of the dispensing unit.

Figure 25:
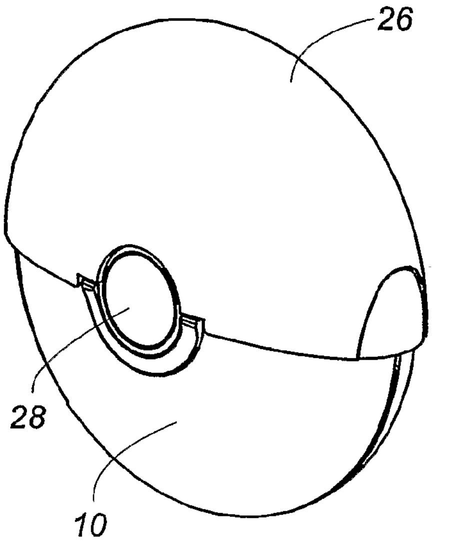
FIG. 25 is a perspective view of the above device with an outer cover attached.
Figure 26:
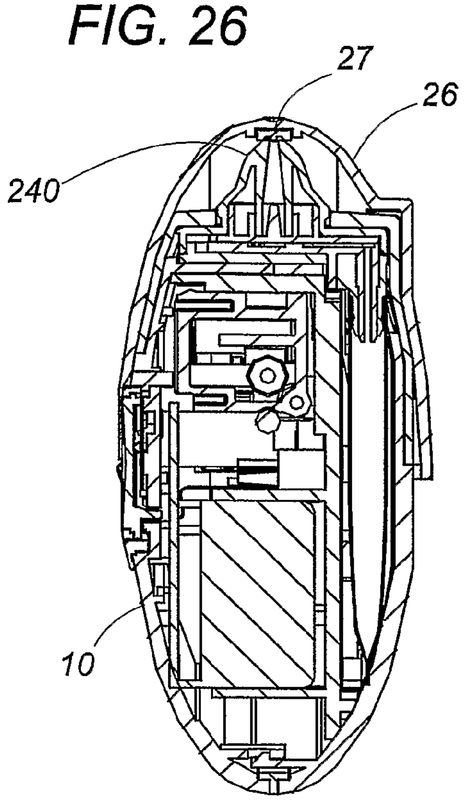
FIG. 26 is a vertical section of the above device with the outer cover attached.

In a preferred embodiment, when the outer cover 26 is fitted over the housing 10, as shown in FIGS. 25 and 26, a sealing rubber 27 at the inner upper end of the outer cover 26 comes into contact with the nozzle 240. The outer cover 26 is also formed with tabs 28 one of which conceals therebehind the power switch 60 to keep the device inoperative. Also, the outer cover 26 conceals the release buttons 109 therebehind to prevent accidental detachment of the inner cover from the housing 10.

Figure 27:
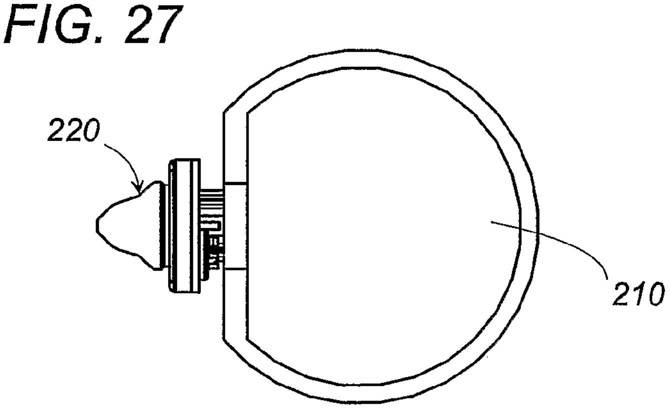
FIG. 27 is a plan view of the cartridge.
Figure 28:
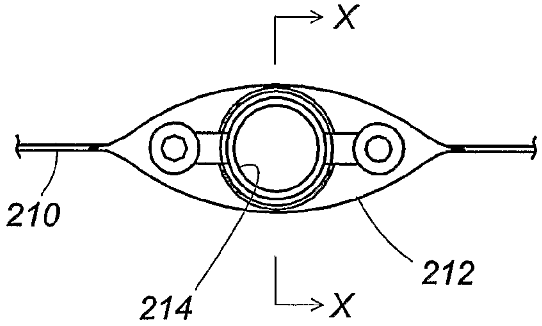
FIG. 28 is a front view of a fitment attached to a reservoir of the cartridge.
Figure 29:
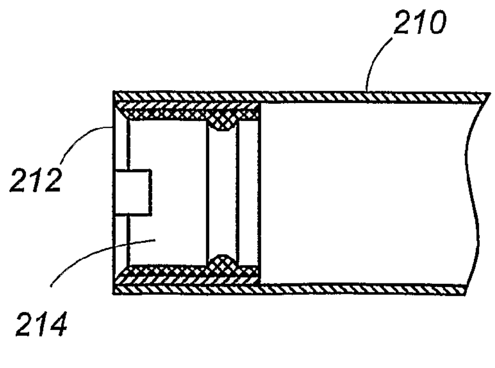
FIG. 29 is a cross section taken along line X-X of FIG. 28.

With reference to FIGS. 27 to 29, the cartridge 200 is again explained in details with respect to geometrical configuration of the reservoir 210. One preferred embodiment of the reservoir as shown as 210 is made from a deformable plastic material into a flat bag which has a planar configuration of a segment of an approximate circle and has a mouth to which the fitment 212 is attached. The fitment 212 is molded from a plastic material to have a socket 214 for removably receiving the plug 232 of the dispensing unit 220. In detail, the reservoir 210 is shaped into the segment of circle defined between a chord and a circumference of an approximate circle greater than a circumference of a semicircle. The mouth or the fitment 212 is located at a center of the chord such that the distance from the mouth to any point of the circumference of the circle can be made approximately the same, providing smooth sucking up of the liquid composition from the reservoir and deforming according to the amount of liquid composition left in the reservoir, such that residue left in the end can be kept to a minimum.

Figure 30:
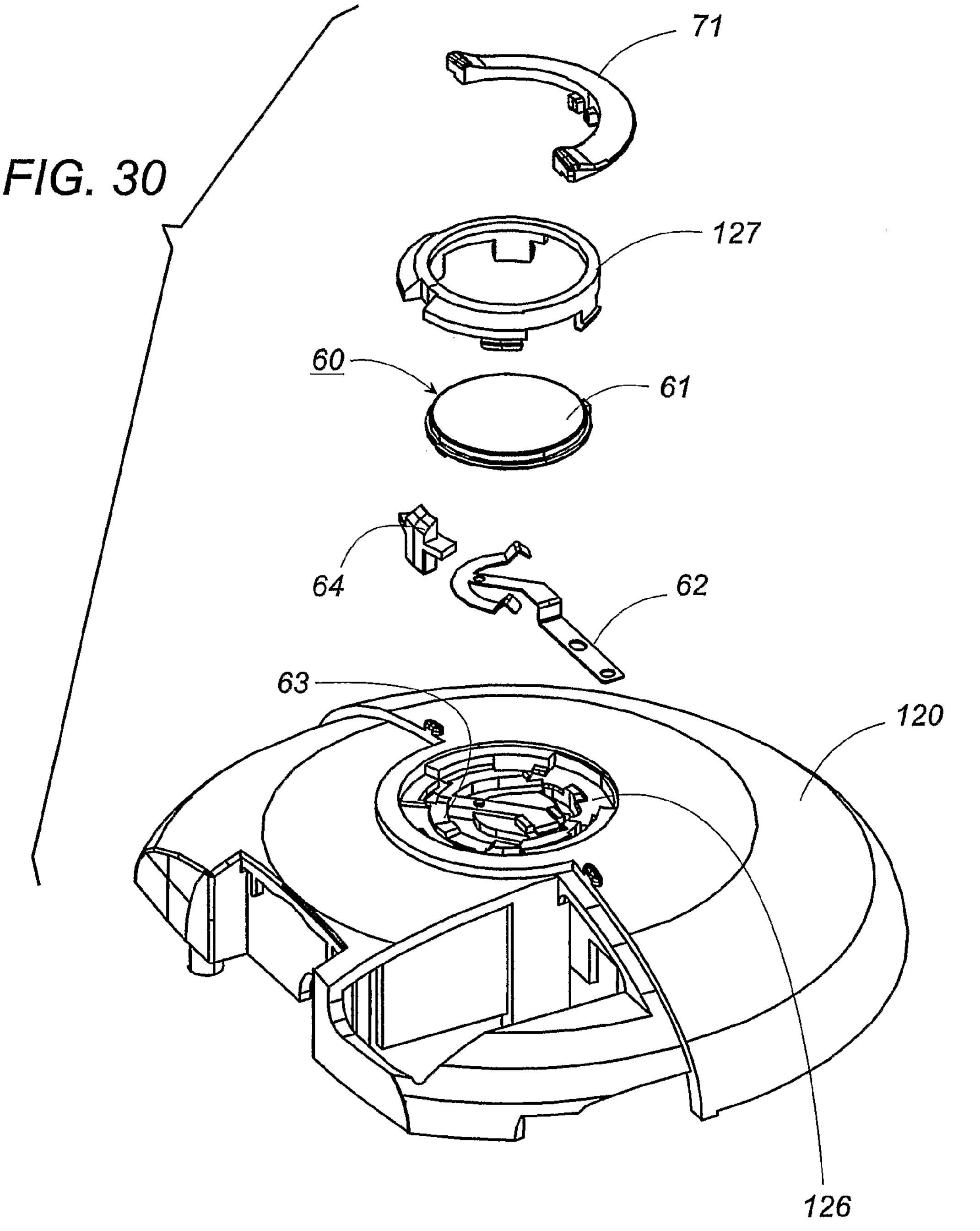
FIG. 30 is an exploded perspective view illustrating a switch, a selector, and associated parts of the device.
Figure 31A:
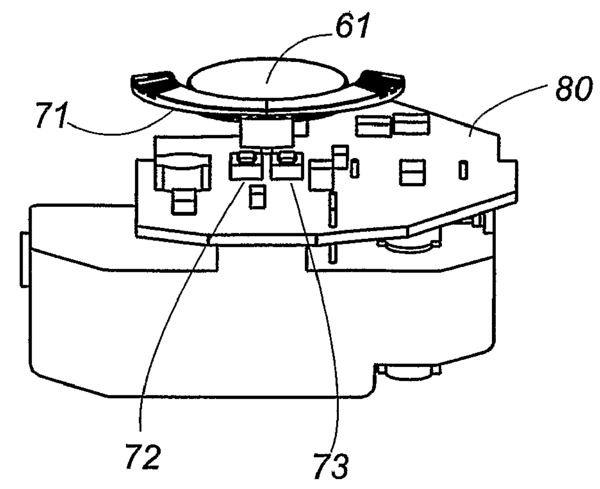
FIGS. 31A to 31C illustrate different positions of the selector, respectively.
Figure 31B:
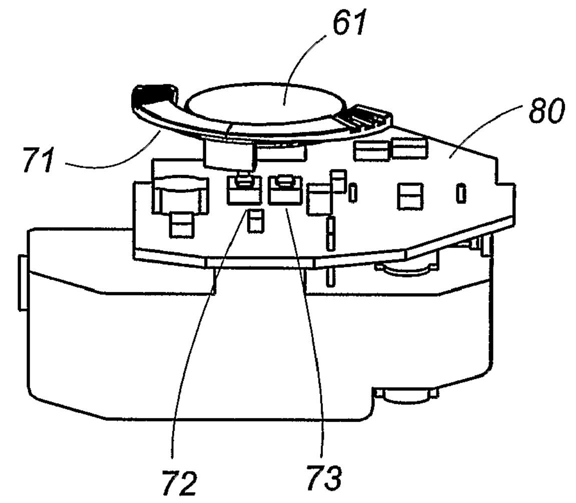
Figure 31C:
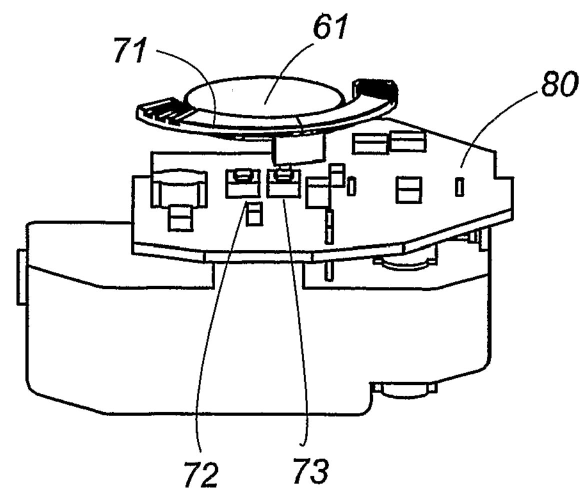

Referring to FIG. 30, the power switch 60 preferably includes a switch knob 61 and a switch contact 62 disposed within a center cavity 126. The switch knob 61 is held within the cavity 126 by means of a retainer ring 127 to be capable of being depressed against a spring bias, and energizes the motor 30 and the high voltage generator 40 upon being depressed. A light-emitting-diode (LED) 63 disposed in the cavity 126 is energized in response to the knob 61 being depressed to issue a light through a transparent cover 64 for indication of the operation. In a preferred embodiment, the device also includes a selector 70 for selecting one of three modes, i.e., a lock mode for disabling the operation, a spraying mode for enabling the liquid composition to be electrostatically sprayed, and a dripping mode for enabling the liquid composition to be dispensed out of the nozzle without being electrostatically charged. The selector 70 includes a handle 71 which is rotatable around the ring 127 for selecting one of three positions, i.e., a lock position, a spraying position, and a dripping position, as shown in FIGS. 31A to 31C, respectively defining the above lock mode, the spraying mode, and the dripping mode. In the lock position of FIG. 31A, the handle 71 has its portion engaged with the switch knob 61 to prohibit it from being pressed, thereby disabling the operating of the pump as well as the high voltage generator. The selector 70 also includes tact switches 72 and 73 which are arranged on the printed board 80 to be actuated selectively depending upon the position of the handle 71. In the spraying mode of FIG. 31B, the tact switch 72 is activated such that the pump 230 and the high voltage generator 40 are simultaneously activated upon the switch knob 61 being pressed. In the dripping mode of FIG. 31C, the tact switch 73 is activated such that only the pump 230 is activated upon the switch knob 61 being pressed. Although not clearly seen in the figures, the device may further include an indicator showing which one of the dripping and spraying modes is selected for easy confirmation by the user. Such indicator is preferred to be disposed around the selector handle 71.

Figure 32:
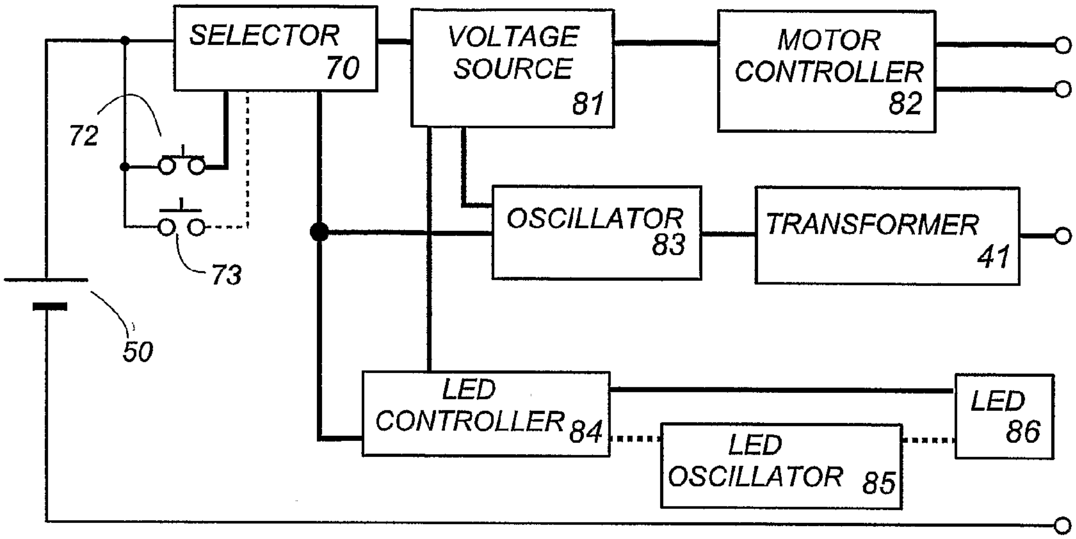
FIGS. 32 and 33 are block diagrams respectively illustrating the operation of a spraying mode and a dripping mode given to the device.
Figure 33:
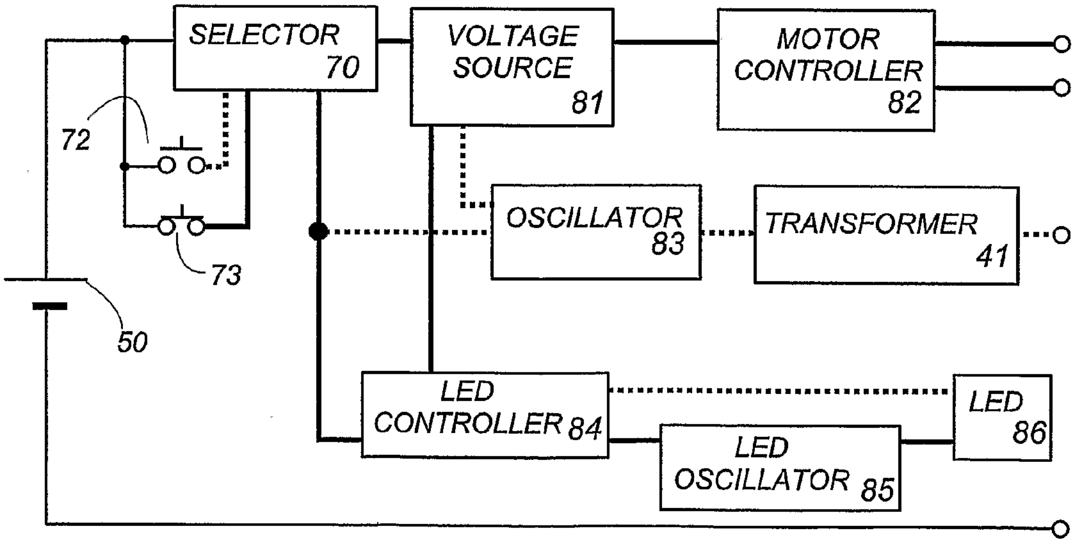

The above operation will be explained also with reference to FIGS. 32 and 33. When the tact switch 72 is turned on by the selector handle 71, the pressing of the knob 61 energizes a voltage source 81, a motor controller 82 and at the same time an oscillator 83 for the transformer 41, thereby activating the motor 30 to operate the pump 230, while applying the high voltage to charge the liquid composition. When, on the other hand, the tact switch 73 is turned on by the selector handle 71, the pressing of the knob 61 energizes the voltage source 81 and the motor controller 82 only for operating the pump without applying the high voltage to the liquid composition. Thus, the user can easily drip the liquid composition by simply manipulating the selector prior to initiating the electrostatic spraying, assuring enhanced convenience of handling the device. The voltage source 81, the motor controller 82, and the oscillator 83 are formed on the printed board 80. Further, the device includes an indicator for indicating which one of the spraying mode and dripping mode is activated. The indicator includes an LED controller 84, an LED oscillator 85, and a LED 86. When the spraying mode is selected at the selector 70, the LED controller 84 acts to turn on the LED 86, as shown in FIG. 32, in response to the knob 61 being pressed. When, on the other hand, the dripping mode is selected at the selector 70, the LED controller 84 drives the LED oscillator 85 to turn on and off the LED 86 intermittently, as shown in FIG. 33, in response to the knob 61 being pressed, thereby providing different visual confirmation to the user for easy distinction between the spraying mode and the dripping mode.

Figure 34:
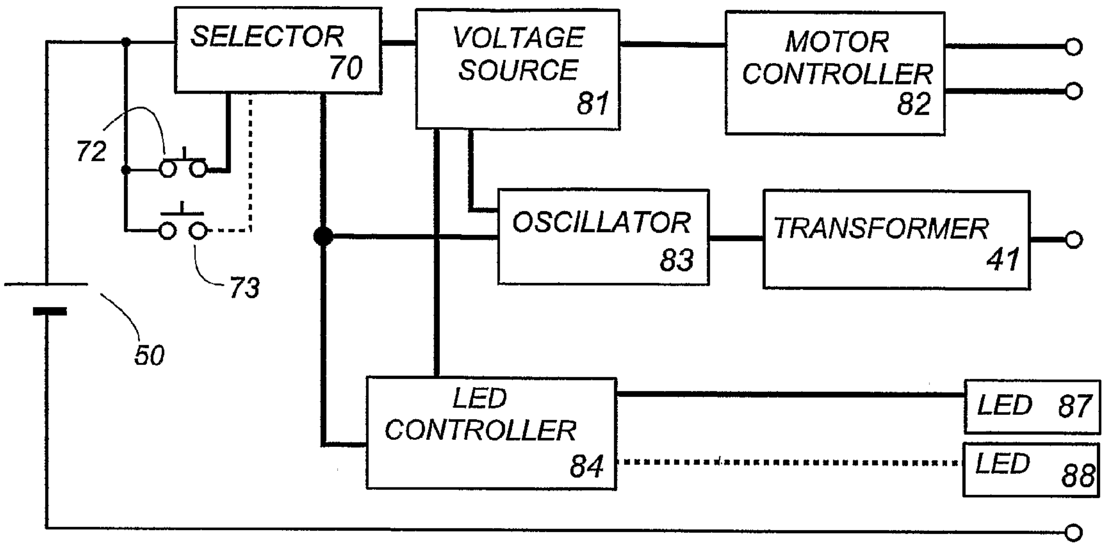
FIGS. 34 and 35 are block diagrams of an indicator respectively illustrating the operation of a spraying mode and a dripping mode given to the device in accordance with a modification of the above embodiment.
Figure 35:
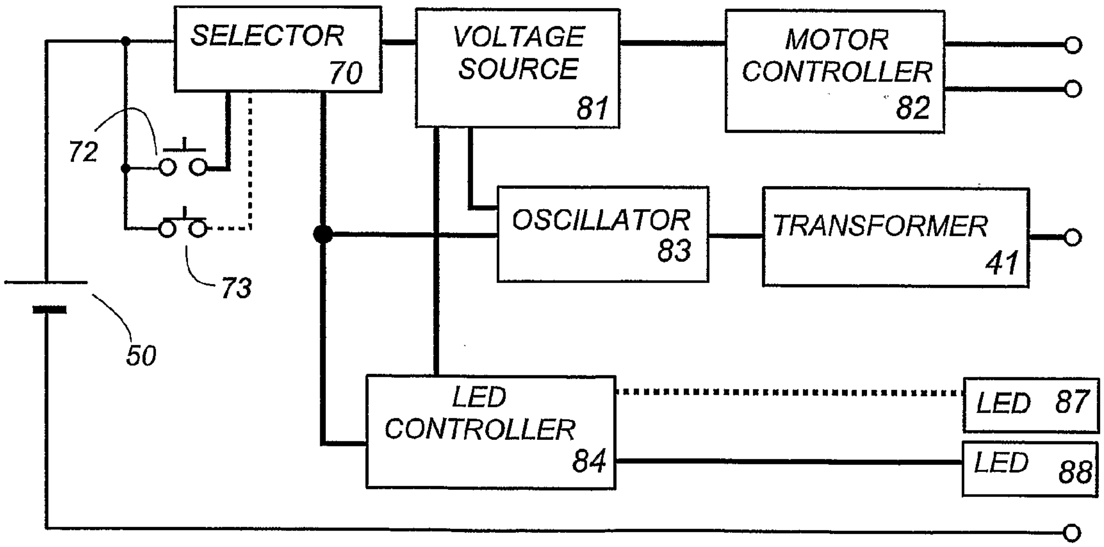

FIGS. 34 and 35 illustrate an alternative indicator using a first LED 87 and a second LED 88 that emit different colors. The first LED 87 is alone turned on by the LED controller 84 when the spraying mode is selected, while only the second LED 88 is alone turned on when the dripping mode is selected.

Figure 36:
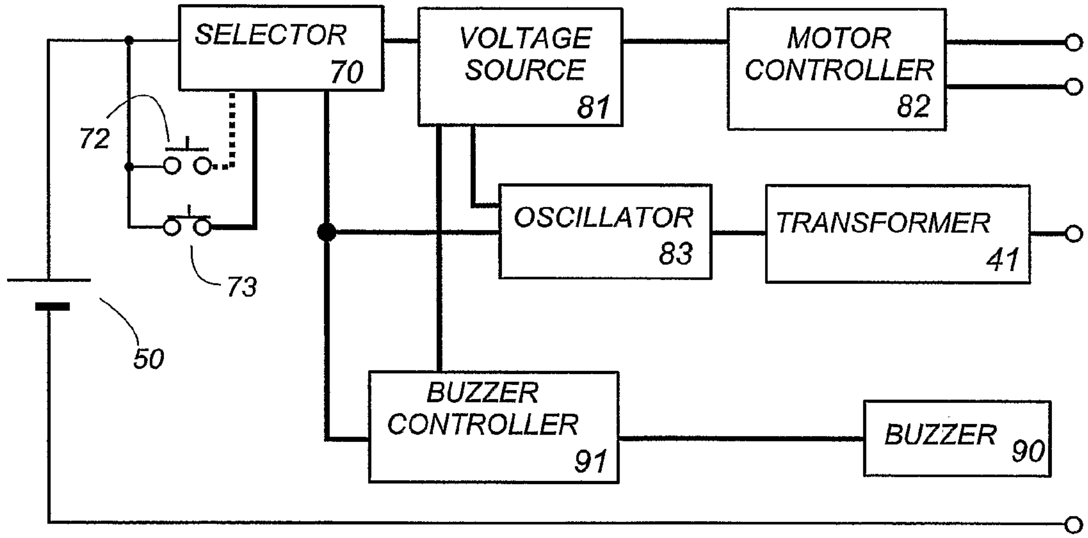
FIG. 36 is a block diagram of an indicator illustrating the operation of a spraying mode and a dripping mode given to the device in accordance with a modification of the above embodiment.

FIG. 36 illustrates a further modification of the indicator using a buzzer 90 and a buzzer controller 91. The buzzer controller 91 is included to shift the sound frequency issued from the buzzer 90 or simply turn on and off the buzzer 90. When the spraying mode is selected, the buzzer controller 91 causes the buzzer 90 to issue the sound of a first frequency or turn off the buzzer 90. When the dripping mode is selected, the buzzer controller 91 causes the buzzer 90 to issue the sound of a second frequency or turn on the buzzer 90.

Figure 37C:
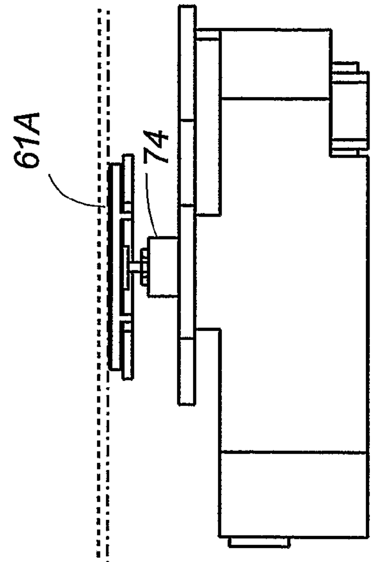
FIGS. 37A to 37C illustrate different positions of a switch for making an analogous function of the selector in accordance with a preferred embodiment of the present invention.
Figure 37B:
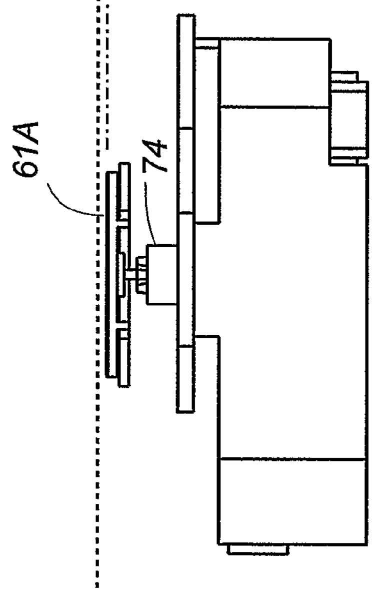
Figure 37A:
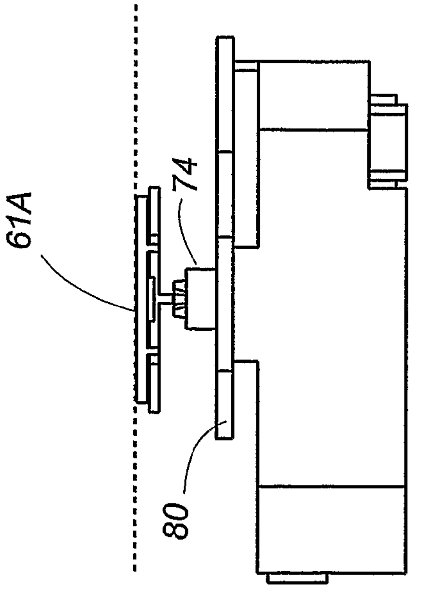

FIGS. 37A to 37C illustrate another scheme of selecting the dripping mode and the spraying mode. In this modification, a tact switch 74 of press-responsive type is cooperative with the switch knob 61A to constitute the power switch added with the function of the selector. That is, the tact switch 74 gives three positions, i.e., an off position of FIG. 37A, a spray mode position of FIG. 37B, and a drip mode position of FIG. 37C. In the off position, the switch 74 is not actuated to disable the operation of the pump as well as the high voltage generator. When the knob 61A is pressed to a small extent to correspondingly depress the switch 74, the spraying mode is selected to energize the pump 230 as well as the high voltage generator 40 for making the electrostatic spraying of the liquid composition. Upon the knob 61A being pressed to a further extent, the switch 74 is correspondingly depressed to select the dripping mode to activate only the pump 230 for dispensing the liquid composition without the electric charge. Thus, the user can easily select the mode by simply varying the pressure applied to the switch knob 61A. Alternatively, the dripping mode and the spraying mode may be assigned respectively to the depression of the small extent and to that of the further extent.

Figure 38:
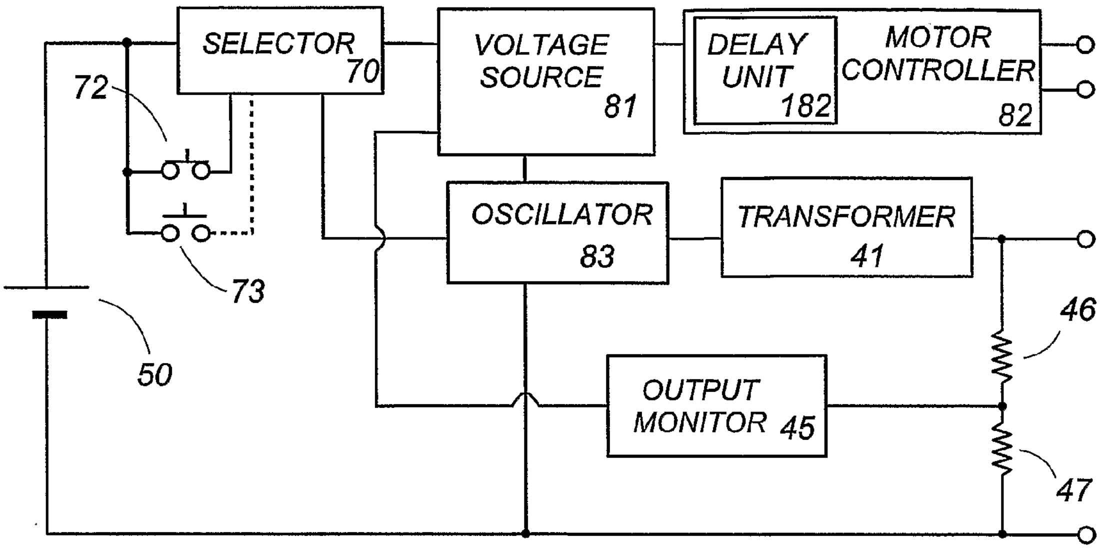
FIG. 38 is a block diagram illustrating the operation of the spraying mode utilized in accordance with another preferred embodiment of the present invention.

FIG. 38 illustrates an electric circuitry incorporated in the device of another preferred embodiment for successfully operating the device in the spraying mode. The circuitry is specifically designed to make the spraying mode successfully and safely. One scheme realized in the circuit is to supply the liquid composition from reservoir 210 to the emitter electrode 250 only after the emitter electrode receives a stabilized high output voltage for successfully charging and spraying the liquid composition. Without being bound by theory, sufficient charging of the area around the emitter electrode prior to spraying is believed to provide good spray quality of the liquid composition at initial usage, as well as usage after the liquid composition is consumed to a certain degree. At initial usage, the liquid composition is delivered to the dispensing unit uncharged. It is believed that advanced charging of the area around the emitter electrode provides sufficient and uniform charge to the liquid composition when delivered to the vicinity for the first time, thereby resulting in a good spray quality. At usage after the liquid composition is consumed to a certain degree, and therefore after the bulk of the liquid composition has gone through a series of charging and decharging, the liquid composition has a tendency to separate and/or generate clumps of solid material. It is believed that, by charging the liquid composition, such separation and clumps are alleviated, thereby providing a liquid composition in the initially intended physicochemical state. The other scheme is to cease the spraying operation when the emitter electrode receives unduly high voltage that may cause an unallowable corona discharging around the emitter electrode and fail to continue the intended electrostatic spraying. Like parts are designated by like reference numerals utilized in the previous embodiment and no duplicate explanation is made for the respective parts.

In order to accomplish the former scheme, the motor controller 82 is configured to include a delay unit 182 which activates the motor 30, i.e., the pump 230 only after a delay of about one second from the time when the high voltage generator generates the stabilized high voltage output. In that the high voltage generator, combination of the oscillator 83 and the transformer 41, is expected to give the stabilized output after an elapse of about few tenths of one second from the time it is energized, the pump is delayed by about one second such that the liquid composition is supplied only after the emitter electrode receives the stabilized voltage output from the transformer 41. The delay unit 182 is composed of a time which starts counting upon being supplied with the power from the voltage source 81 and triggers the motor controller 82 to activate the pump 230. Alternatively, the delay unit 182 may be realized by a delay circuit composed of a resistor and a capacitor.

For accomplishing the latter scheme, the circuitry includes an output monitor 45 for monitoring the voltage output from the transformer 41. The oscillator 83 of the high voltage generator may, for some unpredictable reasons, generate excessively high voltage output from the transformer 41 that causes unacceptable corona discharging around the emitter electrode. In order to eliminate such unacceptable event and to keep the safe operation of the device, the output monitor 45 compares the monitored voltage with a critical level so as to cease activating the oscillator 83 as well as the motor controller 82 when the monitored voltage exceeds the critical level. Thus, the emitter electrode 250 is kept free from the excessively high voltage and therefore from causing the unallowable corona discharging, while the pump 230 or the dispensing unit 220 is disabled to take no superfluous liquid composition from the reservoir 210. The voltage output from the transformer 41 is divided by a voltage divider of resistors 46 and 47 to give a divided voltage to the output monitor 45 as representative of the voltage output.

All documents cited in the Detailed Description of the Invention are, in relevant part, incorporated herein by reference; the citation of any document is not to be construed as an admission that it is prior art with respect to the present invention.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

The invention claimed is:

1. An electrostatic spraying device being configured and disposed to electrostatically charge and dispense a liquid composition from a supply to a point of dispense, wherein the device comprises:

an actuator;

a high voltage generator to provide a high voltage;

a power source to activate said actuator and said high voltage generator;

a reservoir to contain the supply of the liquid composition;

a dispensing unit comprising a pump in immediate downstream relation with the reservoir for supplying the liquid composition from the reservoir, the pump being mechanically connected to said actuator to be driven thereby, an emitter electrode to electrostatically charge the liquid composition, the emitter electrode being electrically connected to said high voltage generator; and a nozzle to dispense the liquid composition, the nozzle being disposed at the point of dispense, a switch for manipulating the power source; and a selector for providing a spraying mode and a dripping mode selectively in response to the switch being manipulated;

wherein the dripping mode is such that said pump is alone actuated to dispense the liquid composition out through the nozzle absent electrical charge, wherein the spraying mode is such that said pump as well as the emitter electrode are simultaneously activated to dispense the liquid composition out through the nozzle with the liquid composition being electrically charged at the emitter electrode prior to exiting the nozzle, wherein said selector comprises a handle, a first tact switch, and a second tact switch, said handle being engaged with a switch knob of said switch to be movable therewith, and having a portion selectively engageable with said first and second tact switches, said first tact switch being mounted on a printed board and connected to operate said high voltage generator and said actuator for executing said spraying mode upon being pressed by said handle, and said second tact switch being mounted on said printed board and connected to operate said actuator for executing said dripping mode upon being pressed by said handle, and wherein said pump is a gear pump which has a pump chamber with a flat base molded from a plastic material, gears in the pump chamber, and a metal plate mounted in the flat base, said metal plate formed with a pin for detachable electrical connection with a voltage terminal provided on the side of the housing to relay the high voltage to the emitter electrode, said emitter electrode and said metal plate being cooperative to charge the liquid composition within the pump chamber.

2. The device as set forth in claim 1, said device includes a housing which carries said actuator, said high voltage generator, said power source, said switch, and said selector.

3. The device as set forth in claim 1, wherein said selector is exposed on the exterior of said housing to be manipulated by the user's finger, said selector being movable between a dripping position defining said dripping mode and a spraying position defining said spraying mode, said selector surrounding said switch in immediately adjacent relation thereto and rotatable about an axis between said dripping position and said spraying position.

4. The device as set forth in claim 3, wherein said selector has a lock position which prohibits said motor and the emitter electrode from being activated.

5. The device as set forth in claim 1, wherein said housing is formed on its exterior with an indicator which indicates which one of said dripping mode and said spraying mode is selected.

6. The device as set forth in claim 1, wherein said spraying mode is arranged to start activating said pump after a delay from activating said high voltage generator.

7. The device as set forth in claim 1, wherein said spraying mode is arranged to include monitoring of the high voltage output from said high voltage generator and to cease activating said high voltage generator and said pump when said monitored high voltage output exceeds a critical level.

8. The device as set forth in claim 1, further including:

an outer cover detachable to a housing carrying said high voltage generator, said power source, said dispensing unit, said reservoir, said switch, and said selector, said outer cover being formed with a tab which conceals therebehind said switch to keep said device inoperative.

9. The device as set forth in claim 2, wherein said dispensing unit is connected to the reservoir to form a removable cartridge detachable to the housing that incorporates, an electric motor for rotating the actuator, the high voltage source, the switch, and the selector, said actuator coming into engagement with the pump when said cartridge is attached to the housing for enabling the operation of the pump.

10. The device as set forth in claim 9, wherein said pump has a plug for detachable connection with said reservoir.

11. The device as set forth in claim 2, wherein said housing is shaped into a flat disc.

12. An electrostatic spraying device being configured and disposed to electrostatically charge and dispense a liquid composition from a supply to a point of dispense, wherein the device comprises:

an actuator;

a high voltage generator to provide a high voltage;

a power source to activate said actuator and said high voltage generator;

a reservoir to contain the supply of the liquid composition;

a dispensing unit comprising a pump in immediate downstream relation with the reservoir for supplying the liquid composition from the reservoir, the pump being mechanically connected to said actuator to be driven thereby, an emitter electrode to electrostatically charge the liquid composition, the emitter electrode being electrically connected to said high voltage generator, and a nozzle to dispense the liquid composition, the nozzle being disposed at the point of dispense; and a switch for manipulating the power source;

wherein said pump is a gear pump which has a pump chamber with a flat base molded from a plastic material, gears in the pump chamber, and a metal plate mounted in the flat base, said metal plate formed with a pin for detachable electrical connection with a voltage terminal provided on the side of the housing to relay the high voltage to the emitter electrode, said emitter electrode and said metal plate being cooperative to charge the liquid composition within the pump chamber.

13. The device as set forth in claim 12, further comprising a selector for providing a spraying mode and a dripping mode selectively in response to the switch being manipulated;

wherein the dripping mode is such that said pump is alone actuated to dispense the liquid composition out through the nozzle absent electrical charge, and wherein the spraying mode is such that said pump as well as the emitter electrode are simultaneously activated to dispense the liquid composition out through the nozzle with the liquid composition being electrically charged at the emitter electrode prior to exiting the nozzle.

14. The device as set forth in claim 13, wherein said device includes a housing which carries said actuator, said high voltage generator, said power source, said switch and said selector.

15. The device as set forth in claim 14, wherein said selector is exposed on the exterior of said housing to be manipulated by the user's finger, said selector being movable between a dripping position defining said dripping mode and a spraying position defining said spraying mode, said selector surrounding said switch in immediately adjacent relation thereto and rotatable about an axis between said dripping position and said spraying position.

16. The device as set forth in claim 15, wherein said selector has a lock position which prohibits said motor and the emitter electrode from being activated.

17. The device as set forth in claim 14, wherein said housing is formed on its exterior with an indicator which indicates which one of said dripping mode and said spraying mode is selected.

18. The device as set forth in claim 13, wherein said spraying mode is arranged to start activating said pump after a delay from activating said high voltage generator.

19. The device as set forth in claim 13, wherein said spraying mode is arranged to include monitoring of the high voltage output from said high voltage generator and to cease activating said high voltage generator and said pump when said monitored high voltage output exceeds a critical level.

20. The device as set forth in claim 12, further including:

an outer cover detachable to a housing carrying said high voltage generator, said power source, said dispensing unit, said reservoir, and said switch, said outer cover being formed with a tab which conceals therebehind said switch to keep said device inoperative.

* * * * *